United States Patent
Bluemli et al.

(10) Patent No.: US 8,562,345 B2
(45) Date of Patent: Oct. 22, 2013

(54) APPARATUS FOR FASTENING A DENTAL PROSTHESIS

(75) Inventors: Markus Bluemli, Biel/Bienne (CH); Hans-Ullrich Stanger, Biel/Bienne (CH); Mathias Strazza, Meinisberg (CH); Jean-Fred Studer, Lamboing (CH)

(73) Assignee: Cendres + Metaux SA, Biel/Bienne (CH)

( * ) Notice: Subject to any disclaimer, the term of this patent is extended or adjusted under 35 U.S.C. 154(b) by 78 days.

(21) Appl. No.: 13/256,645

(22) PCT Filed: Mar. 16, 2010

(86) PCT No.: PCT/CH2010/000072
§ 371 (c)(1),
(2), (4) Date: Sep. 15, 2011

(87) PCT Pub. No.: WO2010/105380
PCT Pub. Date: Sep. 23, 2010

(65) Prior Publication Data
US 2012/0003608 A1 Jan. 5, 2012

(30) Foreign Application Priority Data
Mar. 19, 2009 (CH) ......................................... 412/09

(51) Int. Cl.
*A61C 13/12* (2006.01)
*A61C 13/225* (2006.01)

(52) U.S. Cl.
USPC ....................................................... 433/172

(58) Field of Classification Search
USPC .............. 433/167, 168.1, 169, 171, 172, 173, 433/177, 191, 193, 194, 195, 181–183
See application file for complete search history.

(56) References Cited

U.S. PATENT DOCUMENTS

| 1,367,885 | A | * | 2/1921 | Means | 433/169 |
| 4,209,904 | A | * | 7/1980 | Staubli | 433/177 |
| 5,678,997 | A | | 10/1997 | De Buck | |
| 6,652,278 | B2 | | 11/2003 | Honkura et al. | |
| 2007/0298655 | A1 | * | 12/2007 | Auderset et al. | 439/595 |
| 2009/0269715 | A1 | | 10/2009 | Sprenger | |

FOREIGN PATENT DOCUMENTS

| DE | 1516457 A1 | 1/1970 |
| DE | 4422773 A1 | 1/1996 |
| EP | 1192916 A | 4/2002 |
| WO | 2008034267 A | 3/2008 |

OTHER PUBLICATIONS

International Search Report, dated Jul. 2, 2010, in PCT/CH2010/000072.

* cited by examiner

*Primary Examiner* — Cris L Rodriguez
*Assistant Examiner* — Justin O'Donnell
(74) *Attorney, Agent, or Firm* — Young & Thompson

(57) ABSTRACT

The device for fastening a dental prosthesis includes a bar patrix (20) and a connecting part (10), which can be attached to the dental prosthesis and has a recess into which the bar patrix can be inserted and which is surrounded by two side walls (11, 12) connected via a ceiling element (13). The side walls (11, 12) and the ceiling element (13) are shaped such that the dental prosthesis, when it is placed on the bar patrix (20) via the connecting part (10) attached thereon, rests on the bar patrix via a first (11), a second (12) and a third support location (13*c*), wherein in each case a free space (14*a*, 14*b*) is present between the first and third support locations and the second and third support locations.

17 Claims, 4 Drawing Sheets

APPARATUS FOR FASTENING A DENTAL PROSTHESIS

BACKGROUND OF THE INVENTION (1) Field of the Invention

The present invention relates to an device for fastening a dental prosthesis.

(2) Description of Related Art

Such devices have a connecting part which can be attached to a bar patrix so as to fasten the dental prosthesis thereto in a detachable manner. For this purpose, the connecting part has a recess into which the bar patrix can be inserted (see e.g. WO 2008/034267 A1). As is known, the shape of this recess is adapted to the cross section of the bar matrix in such a manner that a form fit between connecting part and bar patrix is created. However, it was found that such a form fit makes the complete integration of the connecting part difficult and that there is the risk that the connecting part does not rest in an optimal manner against the bar patrix. This can cause that the dental prosthesis moves back and forth in a resilient manner during chewing movements, which gives an annoying feeling.

BRIEF SUMMARY OF THE INVENTION

It is an object of the present invention to provide a device for fastening a dental prosthesis by means of which the hold of the dental prosthesis on a bar patrix is improved.

A device which solves said object is specified in the claim 1. The further claims specify preferred embodiments.

BRIEF DESCRIPTION OF THE SEVERAL VIEWS OF THE DRAWING(S)

The invention is illustrated below by means of exemplary embodiments and with reference to the figures. In the figures.

DETAILED DESCRIPTION OF THE INVENTION

First Exemplary Embodiment

FIGS. 1-4 show a first exemplary embodiment of a device with a bar matrix 10 serving as connecting part and a bar patrix 20. They can be connected to each other in a detachable manner and, for reasons of simplification, are designated hereinafter as matrix and patrix.

Figure 1:
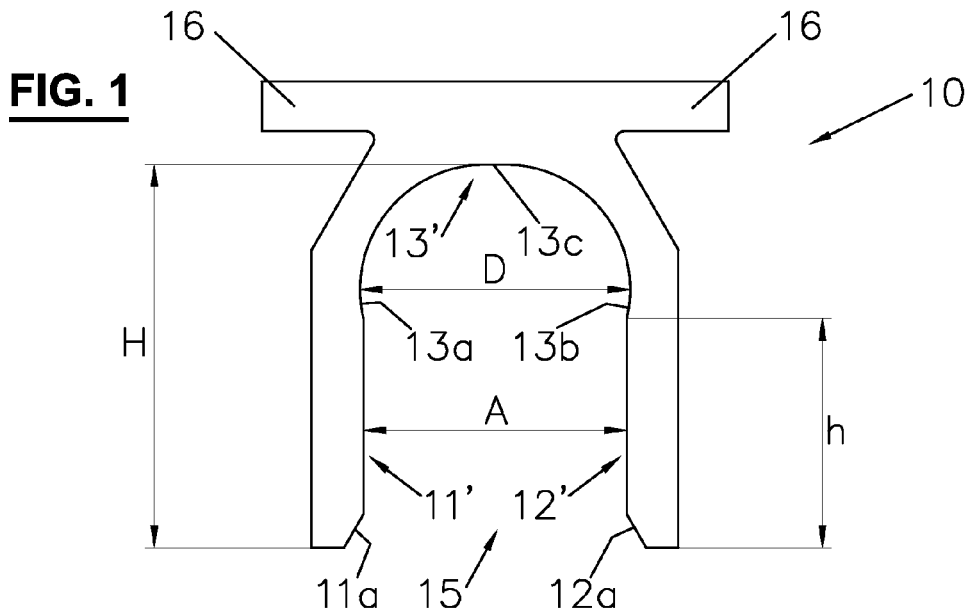
FIG. 1 shows a front view of a bar matrix serving as connecting part according to a first exemplary embodiment of a device according to the invention.

The matrix 10 is formed as elongated housing which comprises side parts (hereinafter also called lamellas) occlusally connected to each other and has a cross-sectional shape as it is shown in FIG. 1. Said matrix 10 is provided with a recess 15 into which the patrix 20 can be inserted and which is defined by two side walls 11' and 12'. The latter are connected to each other via a ceiling element 13' in the form of an arch 13.

The side walls 11', 12' are formed as substantially flat surfaces which are arranged substantially parallel to each other but are beveled at their basal end, whereby a chamfer 11a, 12a is created. Providing the chamfers 11a, 12a facilitates the integration of matrix 10 and patrix 20.

At the transition to the respective side wall 11', 12' the arch 13 has an undercut 13a and 13b, respectively, and, as viewed in cross-section, has a maximum distance D which is greater than the distance A of the side walls 11', 12' in the region of the transition to the undercut 13a, 13. Accordingly, the respective side wall 11', 12' protrudes with respect to the undercut 13a, 13b.

In the present exemplary embodiment, as viewed in cross-section, the arch 13 is composed of two circular arc-shaped sections which each comprise one of the two undercuts 13a, 13b and which are connected to each other via a substantially straight section 13c.

The height h of the respective side wall 11', 12' is selected here such that it is greater than half the depth H of the recess 15, so that h>H/2.

In the present exemplary embodiment, the matrix 10 has laterally protruding retention elements 16 which ensure the secure hold of the matrix on the dental prosthesis. For example, the matrix 10 is fixed to the dental prosthesis by means of a polymerizate. Depending on the design of the matrix 10, the retention elements can also have a different shape than the one shown in FIG. 1.

Figure 2:
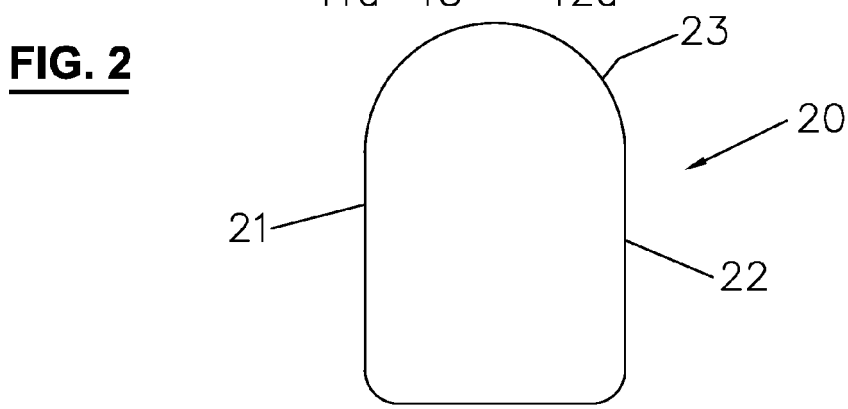
FIG. 2 shows a front view of a bar patrix according to the first exemplary embodiment.

As shown in FIG. 2, the patrix 20 is a Dolder bar which, as viewed in cross-section, is substantially U-shaped. Accordingly, the patrix 20 has two side walls 21 and 22 connected via a bend 23.

Figure 3:
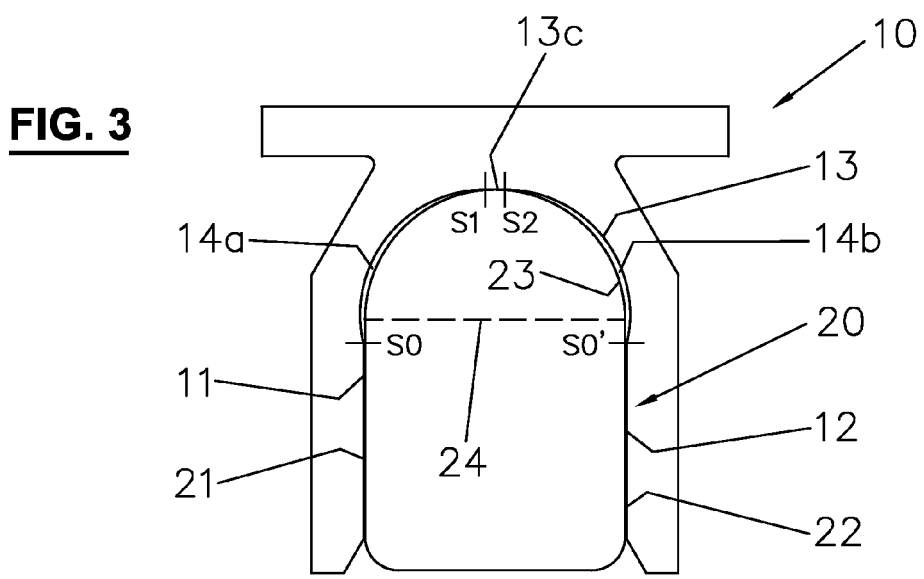
FIG. 3 shows the bar matrix according to FIG. 1 and the bar patrix according to FIG. 2 in the connected state.

FIG. 3 shows the situation when the patrix 20 is inserted into the recess 15 of the matrix 10. The first side wall 11' of the matrix 10 forms a first support location 11 which touches the first side wall 21 of the patrix 20. The second side wall 12' of the matrix 10 forms a second support location 12 which touches the second side wall 22 of the patrix 20. Furthermore, the section 13c of the arch 13 forms a third support location which in the present exemplary embodiment touches the apex of the bend 23 of the patrix 20.

Due to the selected shape of the arch 13, a free space 14a, 14b is created in each case between the first 11 and the third support location 13c as well as the second 12 and the third support location 13c. Accordingly, there is no complete form fit between matrix 10 and patrix 20, but the arch 13 has an oversize so that it runs partially spaced apart from the bend 23. The three support locations 11, 12 and 13c form a three-location support of the matrix 10 on the patrix 20.

In FIG. 3, S0 and S0' indicate the level above which the free space 14a, 14b extends while the path between S1 and S2 defines the length L2 of the third support location 13c. The free space 14a thus extends over a length L1 reaching from S0 to S1 and accordingly, the free space 14b extends over a length L1' reaching from S0' to S2. As shown, L1 and L1' are each greater than L2.

As further shown in FIG. 3, the level defined by S0 and S0' is closer to the end level up to which the recess 15 extends than to the start level where the recess 15 starts. (See FIG. 1 in which the height h corresponds to the level defined by S0 and S0' and the height H indicates the difference between the end level of the recess 15 and the start level of the same.)

Figure 4:
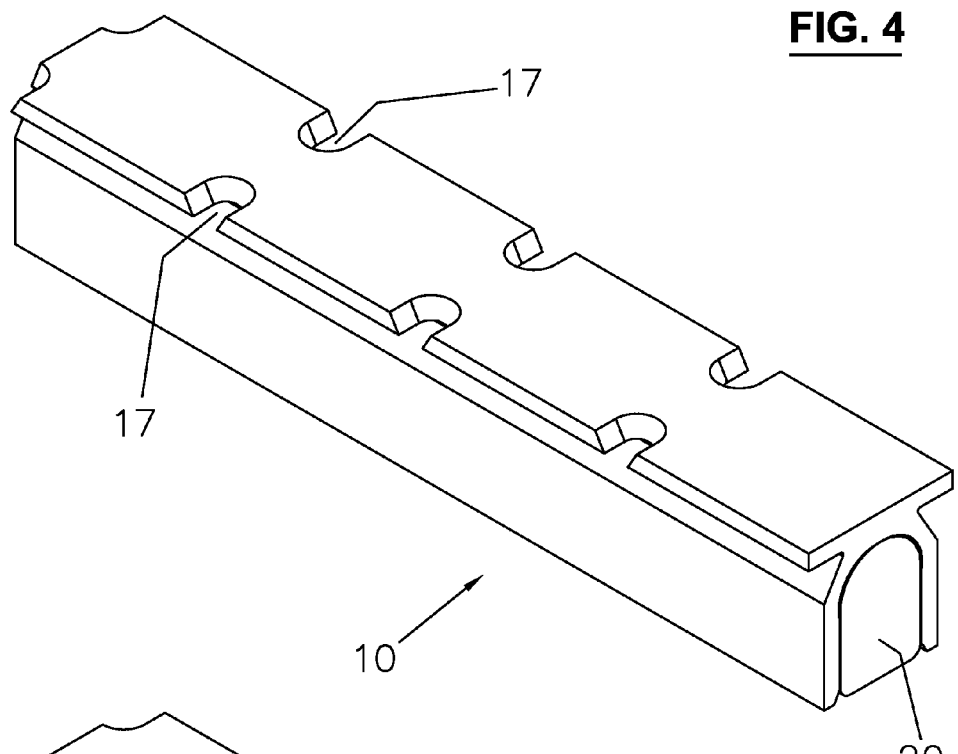
FIG. 4 shows a perspective view of bar matrix and bar patrix according to FIG. 3.
Figure 5:
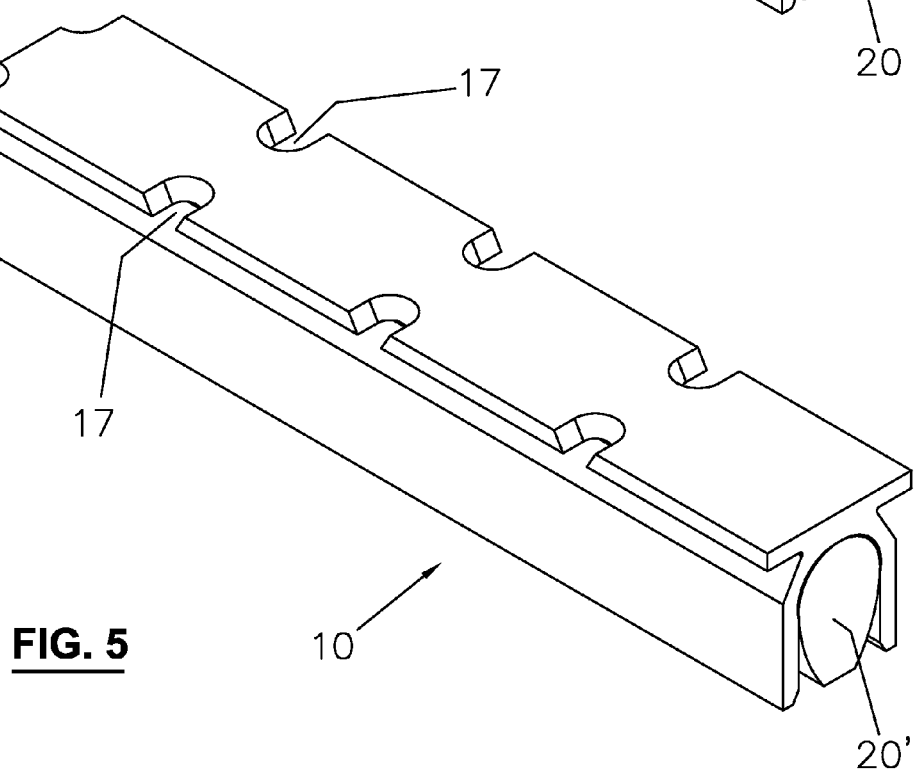
FIG. 5 shows a perspective view of a second exemplary embodiment of a device according to the invention.

FIG. 4 shows a perspective view of the matrix 10 placed onto the patrix 20. As shown, in the present exemplary embodiment, the matrix has markings 17 on the occlusal side. Said markings are formed here in the form of incisions which are arranged at regular distances and extend transverse to the longitudinal direction of the matrix 10. The markings define possible positions for cutting the matrix 10 so as to obtain several pieces of the desired length.

Matrix 10 and patrix 20 according to the first exemplary embodiment form a bar attachment. The friction which can be generated between the walls 11' and 21 as well as the walls 12' and 22 determines the holding force by means of which the matrix 10 is held on the patrix 20. The holding force is given, among other things, by the selected height h and can be adjusted within certain limits by changing the inclination of the side walls 11' and 12' by means of a suitable instrument in such a manner that they slightly narrow or widen conically toward the ends ("activation" and "deactivation", respectively).

Due to the selected shape of the recess 15 with the free spaces 14a, 14b, the matrix 10 rests at three support locations 11, 12, 13c against the patrix 20. The position of said support locations can be precisely specified. In the present example, the position is selected such that the support locations 11 and 12 are located below the level where the bend 23 of the patrix 20 ends. This level is indicated in FIG. 3 by the dashed line 24. Accordingly, the respective free space 14a, 14b reaches above the level 24, and the support locations 11 and 12 rest against the side walls 21 and 22 of the patrix 20.

The transition of the free space 14a, 14b to the support location 11, 12 defines substantially the place where a force transmission of the patrix 20 to the side walls 11', 12' can take place. This place hardly shifts even if a different holding force is set and is located close to the occlusal end of the matrix 10, whereby the lever arm for the force transmission can be kept small.

The shape of the recess 15 further ensures that the patrix 20 can be received therein such that the matrix 10 is prevented from lifting off the patrix 20. Thus, under a load, no undesired resilient movement between matrix 10 and patrix 20 occurs, not even if a strong activation has been selected. In contrast, in case of the known bar attachments which provide a complete form fit between matrix and patrix, it is possible that when integrating the dental prosthesis, the matrix does not reach its end position with respect to the patrix and is moved back and forth relative to the patrix during loading and unloading.

Second Exemplary Embodiment

Instead of the bar attachment according to the first exemplary embodiment which allows a rigid connection between matrix and patrix, the bar matrix 10 can also be used for different types of bar patrixes. FIGS. 5-8 show a second exemplary embodiment of a device having a bar matrix 10 and a bar patrix 20' for forming a bar joint according to Dolder.

Figure 6:
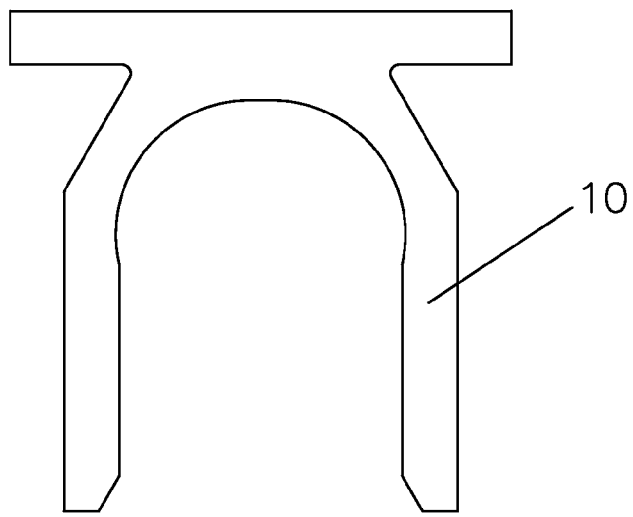
FIG. 6 shows a front view of the bar matrix according to FIG. 5.

The matrix 10 which is shown again in FIG. 6 corresponds to the matrix according to the first exemplary embodiment.

Figure 7:
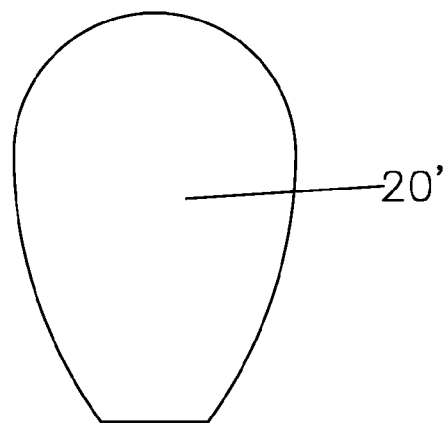
FIG. 7 shows a front view of the bar patrix according to FIG. 5.

The cross-section of the patrix 20' is egg-shaped as shown in FIG. 7. At the apex, the contour has a circular bend which transitions at each of its two ends into a bend with a larger curvature. The level where said circular bend ends is indicated in FIG. 8 by the dashed line 24'.

Figure 8:
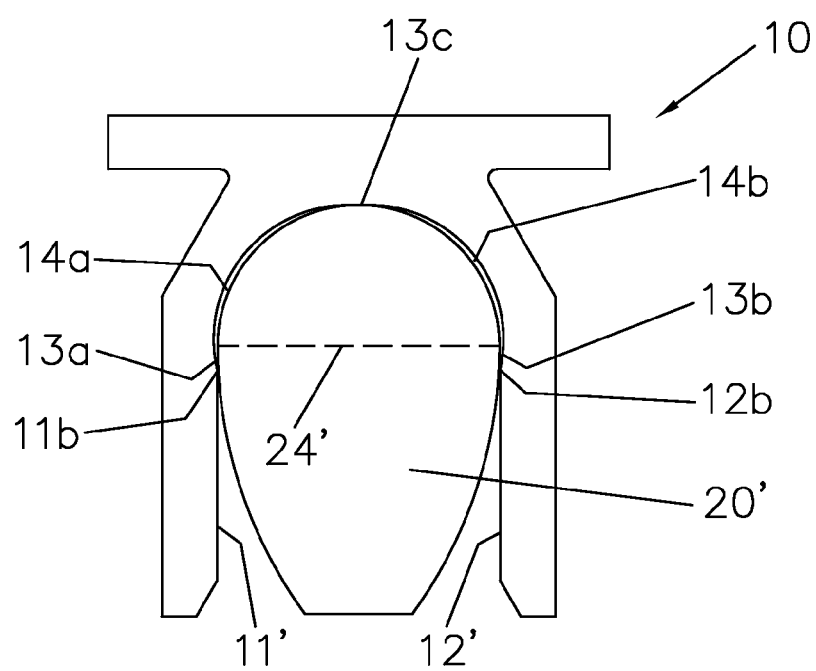
FIG. 8 shows the bar matrix according to FIG. 6 and the bar patrix according to FIG. 7 in the connected state.

Once the matrix 10 is placed onto the patrix 20', three support locations 11b, 12b, 13c are obtained as indicated in FIG. 8. The first location, 11b, and the second support location, 12b, are obtained at the transition from the side wall 11', 12' to the undercut 13a, 13b. The support locations 11b and 12b are below the level 24'. The section 13c of the arch 13 forms the third support location which rests against the apex of the patrix 20'. Between the support locations 13a and 13c as well as between the support locations 13b and 13c, a free space 14a, 14b is created in each case in a similar manner as in the case of the first exemplary embodiment. However, in contrast thereto, not the entire side wall 11', 12' rests against the patrix 20' but only a small portion thereof.

When integrating the matrix 10, the support locations 13a and 13b are moved across the level 24' which defines the widest location of the patrix 20', which finally results in that the lamellas of the matrix 10 snap in place on the patrix 20'. Said snapping in, in addition to the friction, determines the holding force by means of which the matrix 10 is held on the patrix 20'.

As in the first exemplary embodiment, the three support locations 11b, 12b and 13c provide a three-location support which ensures that during the integration, the matrix 10 reaches its end position and is not lift off again from said position. Thereby it is avoided that when subjected to a load, a resilient relative movement between matrix 10 and patrix 20' occurs. However, as a bar joint, the matrix 10 can be moved with respect to the patrix 20' about the longitudinal axis of the same. In this case, the support locations 13a, 13b, 13c shift correspondingly along the patrix 20'.

Third Exemplary Embodiment

Figure 9:
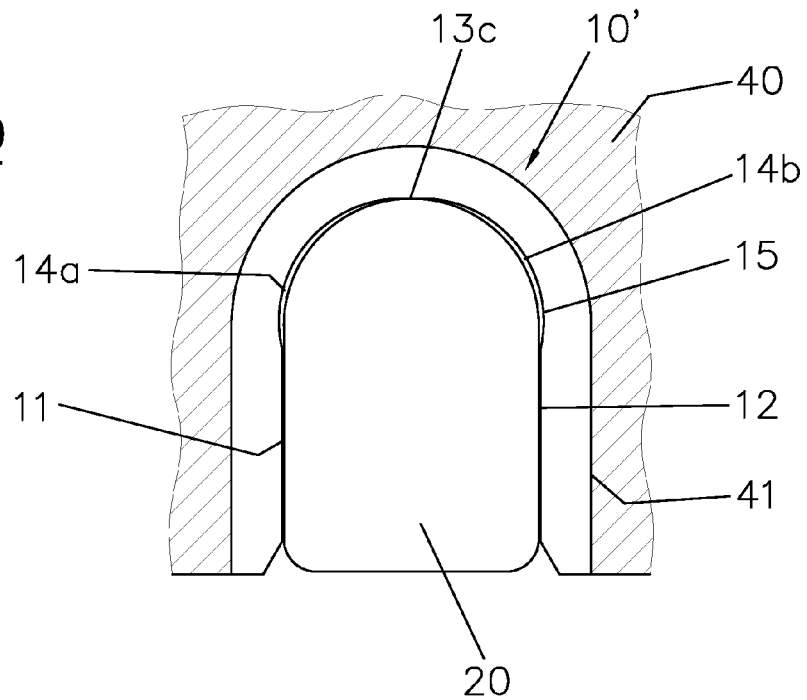
FIG. 9 shows a partial sectional front view of a third exemplary embodiment of a device according to the invention.

FIG. 9 shows a variant of the first exemplary embodiment, wherein the matrix is formed directly in the dental prosthesis 40 and an insert 10' serves as connecting part so as to fasten the dental prosthesis to the bar patrix 20. The insert 10' is inserted in a removable manner in a cut-out 41 which is formed in the dental prosthesis 40. The latter is configured e.g. as prosthesis with a plastic part in which the cut-out 41 is provided during manufacturing.

The insert 10' is formed as an elongated connecting part which extends along the bar patrix 20 and is provided with a recess 15 which is shaped in the same manner as in the first exemplary embodiment. Thus, between the bar patrix 20 and the insert 10', support locations 11, 12, 13c are formed via which the dental prosthesis 40 rests on the bar patrix 20. Between the support locations 11 and 13c as well as 12 and 13c, the free spaces 14a and 14b are created.

As an alternative to the third exemplary embodiment it is conceivable to provide the three support locations 11, 12, 13c and the free spaces 14a, 14b between the dental prosthesis 40 and the insert 10' in that the outer shape of the insert 10' and/or the cut-out 41 of the dental prosthesis 40 are shaped in a suitable manner.

Fourth Exemplary Embodiment

Figure 10:
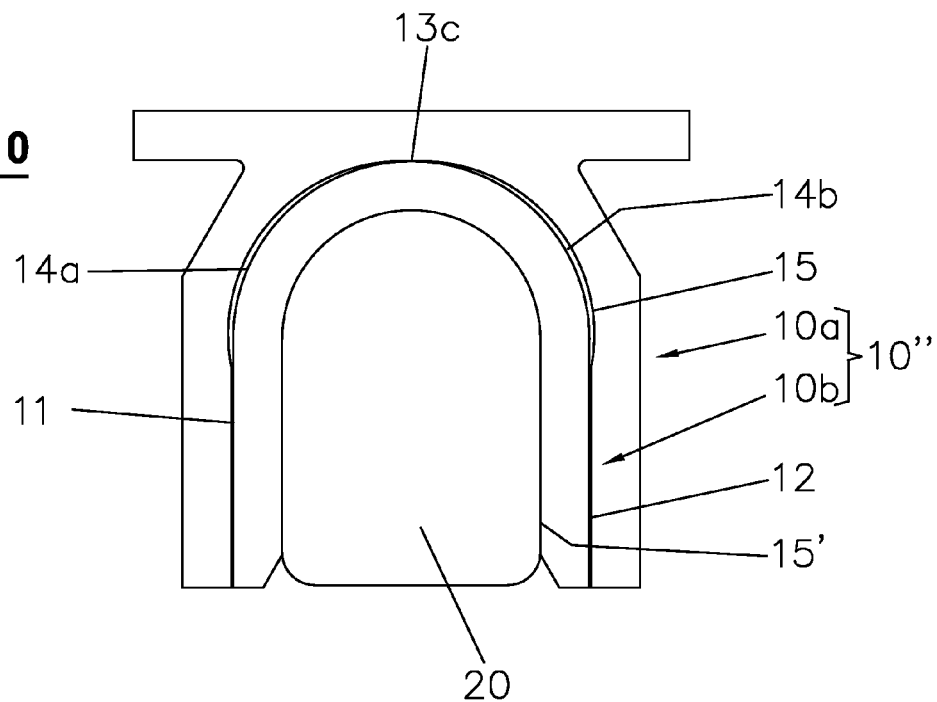
FIG. 10 shows a front view of a fourth exemplary embodiment of a device according to the invention.

FIG. 10 shows a further variant of the first exemplary embodiment, wherein the bar matrix 10" is of a multi-part design. The bar matrix 10" has a matrix housing 10a in which the insert 10b is inserted in a removable manner.

The insert 10b has a recess 15' in which the bar patrix 20 is inserted and which is formed in the present exemplary embodiment in such a manner that the insert 10b rests on the bar patrix 20 in a form fitting manner.

The matrix housing 10a has a recess 15 in which the bar patrix 20 is inserted together with the insert 10b. The recess 15 is shaped in the same manner as in the first exemplary embodiment. Thus, between the matrix housing 10a and the insert 10b, support locations 11, 12, 13c are formed via which the dental prosthesis can rest on the bar patrix 20. Between the support locations 11, 12, 13c, the free spaces 14a, 14b are created.

As an alternative to the fourth exemplary embodiment it is conceivable to provide the three support locations 11, 12, 13c and the free spaces 14a, 14b between the insert 10b and the bar patrix 20 in that the inner shape of the insert 10b, i.e. the recess 15' is shaped in a suitable manner. In this case, a form fitting connection can be provided between the matrix housing 10a and the insert 10b.

The parts 10, 10', 10a, 10b, 20, 20' can each be made as one piece or as a multi-part design and can be prefabricated. They consist of a material which is durable in an oral environment, for example a suitable metal such as titanium, or plastic.

The shape of the recess 15 can be generated e.g. by milling by guiding the tool in the longitudinal direction of the matrix 10. This can be carried out e.g. in a plurality of process steps by first milling a U-shaped cut-out and subsequently generating the two undercuts 13a, 13b by means of a spherical tool.

The respective part 10, 10', 10a, 10b can be manufactured as a long profiled rod from which the user can cut in each case a piece with the desired length.

It is also conceivable to provide the matrix housing 10, 10a and/or the bar patrix 20, 20' as a mold, which can be burnt out, e.g. from plastic or wax, in order to produce the finished part by means of casting.

From the preceding description, numerous modifications are accessible for the person skilled in the art without departing from the scope of the invention which is defined by the claims.

For example, the bar patrix does not necessarily have to be shaped as shown in the figures. Its cross-section can also have a different convex shape, e.g. a rectangular or a more generic shape. Furthermore, the bar patrix can be provided for example at the ends with means for fastening on implants or natural teeth.

The arch 13 and the side walls 11', 12' do not have to be shaped as illustrated in the figures. The section 13c, e.g., can be straight or curved and/or the respective side wall 11', 12' can be flat or curved.

As viewed in cross-section, the length over which the third support location 13c extends can be selected as small as desired (cf. the distance between S1 and S2 in FIG. 3). If need be, the length can be extremely small so that the support location 13c, as viewed in cross-section, is virtually point-shaped.

The invention claimed is:

1. A device for fastening a dental prosthesis, comprising a bar patrix and a connecting part which can be attached to the dental prosthesis and has a recess into which the bar patrix can be inserted and which is surrounded by two side walls (11, 12) which are connected via a ceiling element (13), wherein the side walls and the ceiling element are shaped such that the dental prosthesis, when placed onto the bar patrix by means of the connecting part attached thereon, rests on the bar patrix via a first support location, a second support location, and a third support location, wherein, as viewed in cross-section, a first free space extends over a first length from the first support location to the third support location, and a second free space extends over a second length from the second support location to the third support location, and the third support location extends over a third length, the third length being smaller than the first length and smaller than the second length, and wherein the ceiling element has undercuts for at least partially forming the free spaces.

2. The device according to claim 1, wherein as viewed in cross-section, the respective free space extends above a level which is arranged closer to an end level up to which the recess reaches than to a start level where the recess starts.

3. The device according to claim 1, wherein the ceiling element has an arch with a cross-section which has at least one of a substantially circular arc-shaped section, and at least one substantially straight section (13c).

4. The device according to claim 1, wherein,
the recess comprises a depth, and
a height of the side walls is greater than half the depth of the recess.

5. The device according to claim 1, wherein,
the bar patrix, as viewed in cross-section, has a bend which extends from a first point to a second point, a line going through the first point and the second point defining a level,
the third support location, as viewed in cross-section, is arranged at one side of the level, and the first support location and the second support location are arranged at the other side of the level.

6. The device according to claim 1, wherein the connecting part has beveled surfaces at a basal end.

7. The device according to claim 1, wherein the side walls each have a surface arranged substantially parallel to each other.

8. The device according to claim 1, wherein the third support location is located at an apex of the bar patrix.

9. The device according to claim 1, wherein the bar patrix has a cross-section which is convex.

10. The device according to claim 1, wherein the free spaces are formed between the connecting part and the bar patrix.

11. The device according to claim 1, wherein the connecting part is made as one piece or is formed as matrix housing with a removable insert.

12. The device according to claim 1, wherein the connecting part has markings which define positions for dividing the connecting part.

13. The device according to claim 1, wherein the bar patrix has a cross-section which is U-shaped.

14. The device according to claim 1, wherein the bar patrix has a cross-section which is egg-shaped.

15. The device according to claim 1, wherein the bar patrix has a cross-section which is rectangular.

16. The device according to claim 1, wherein the free spaces are formed between a matrix housing and an insert inserted therein, wherein the matrix housing and the insert serve as connecting part.

17. The device according to claim 1, wherein the free spaces are formed between the connecting part and the dental prosthesis.

* * * * *

UNITED STATES PATENT AND TRADEMARK OFFICE
CERTIFICATE OF CORRECTION

PATENT NO. : 8,562,345 B2  Page 1 of 1
APPLICATION NO. : 13/256645
DATED : October 22, 2013
INVENTOR(S) : Bluemli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 73 days.

Signed and Sealed this

Fifteenth Day of September, 2015

Michelle K. Lee
*Director of the United States Patent and Trademark Office*